US009718856B2

(12) United States Patent
Chtourou et al.

(10) Patent No.: US 9,718,856 B2
(45) Date of Patent: Aug. 1, 2017

(54) METHOD FOR PREPARING A CONCENTRATE OF POLYVALENT IMMUNOGLOBULIN

(75) Inventors: Abdessatar Chtourou, Elancourt (FR); Damien Bataille, Ormoy (FR); Georges Michaux, St Remy les Chevreuse (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 152 days.

(21) Appl. No.: 14/131,944

(22) PCT Filed: Jul. 11, 2012

(86) PCT No.: PCT/EP2012/063549
§ 371 (c)(1),
(2), (4) Date: Jan. 10, 2014

(87) PCT Pub. No.: WO2013/007740
PCT Pub. Date: Jan. 17, 2013

(65) Prior Publication Data
US 2014/0141021 A1    May 22, 2014

(30) Foreign Application Priority Data

Jul. 11, 2011    (FR) .................................... 11 56285

(51) Int. Cl.
*C07K 1/36*    (2006.01)
*C07K 16/02*    (2006.01)
*C07K 1/16*    (2006.01)
*C07K 1/30*    (2006.01)
*C07K 16/06*    (2006.01)

(52) U.S. Cl.
CPC ................ *C07K 1/36* (2013.01); *C07K 16/06* (2013.01); *C07K 16/065* (2013.01); *C07K 1/165* (2013.01); *C07K 1/30* (2013.01)

(58) Field of Classification Search
None
See application file for complete search history.

(56) References Cited

U.S. PATENT DOCUMENTS

| | | |
|---|---|---|
| 4,764,369 A | 8/1988 | Neurath et al. |
| 5,075,425 A | 12/1991 | Kotitschke et al. |
| 5,935,442 A | 8/1999 | Lihme et al. |
| 6,069,236 A | 5/2000 | Burnouf-Radosevich et al. |
| 7,041,798 B1 | 5/2006 | Kothe et al. |
| 7,186,410 B2 | 3/2007 | Chtourou et al. |
| 7,553,938 B2* | 6/2009 | Buchacher ........... C07K 16/065 424/176.1 |
| 8,153,382 B2 | 4/2012 | Chtourou et al. |
| 2003/0152966 A1 | 8/2003 | Alred et al. |
| 2004/0132979 A1 | 7/2004 | Chtourou et al. |
| 2007/0299251 A1* | 12/2007 | Lihme ...................... C07K 1/16 530/416 |
| 2009/0074749 A1* | 3/2009 | Chtourou ............... C07K 16/34 424/130.1 |
| 2010/0330071 A1* | 12/2010 | Teschner et al. .......... 424/130.1 |

FOREIGN PATENT DOCUMENTS

| | | |
|---|---|---|
| EP | 0 703 922 B1 | 4/1996 |
| EP | 1 385 886 B1 | 2/2004 |
| JP | 2005-500265 A | 1/2005 |
| WO | WO-02/092632 A1 | 11/2002 |
| WO | WO-2005/073252 A1 | 8/2005 |
| WO | WO-2007/077365 A2 | 7/2007 |
| WO | WO-2011/131786 A2 | 10/2011 |

OTHER PUBLICATIONS

Johansson et al. "Preparation and characterization of prototypes for multi-modal separation aimed for capture of positively charged biomolecules at high-salt conditions" J Chromatogr A, 1016(1), pp. 35-49, 2003.*
Arpanaei et al. "Improved expanded bed adsorption chromatography systems" Technical university of Denmark, Ph.D. thesis, published 2007, pp. 1-173.*
Search Report for Taiwanese Application No. 101124715 dated May 22, 2014.
Buchacher et al., "Purification of intravenous immunoglobulin G from human plasma—aspects of yield and virus safety," Biotechnology Journal, vol. 1, 2006, pp. 148-163.
Cohn et al., "Preparation and Properties of Serum and Plasma Proteins. IV. A System for the Separation in Fractions of the Protein and Lipoprotein Components of Biological Tissues and Fluids," J. Am. Chem., vol. 68, 1946, pp. 459-475.
Haute Autorite de Sante (HAS)—Commission de la Transparence, "Avis: Clairyg 50 mg/mL, solution pour perfusion," Feb. 10, 2010, 10 pages, XP-002667349.
International Search Report for International Application No. PCT/EP2012/063549 dated Aug. 8, 2013.
Lebing et al., "Properties of a new intravenous immunoglobulin (IGIV-C, 10%) produced by virus inactivation with caprylate and column chromatography," Vox Sanguinis, S. Karger AG, Basel CH, vol. 84, No. 3, Apr. 1, 2003, pp. 193-201.

(Continued)

Primary Examiner — Daniel E Kolker
Assistant Examiner — James Rogers
(74) Attorney, Agent, or Firm — Rouget F. Henschel; Potomac Law Group, PLLC

(57) ABSTRACT

The present invention relates to a method for preparing a concentrate of polyvalent immunoglobulins with view to therapeutic use, from an initial solution of blood plasma or a plasma fraction enriched with immunoglobulins, comprising the steps for removing the protein contaminants by precipitation with caprylic acid in order to obtain a solution free of proteases, and for separating by chromatography on a fluidized bed the solution free of proteases, said method allowing a concentrate of human polyvalent immunoglobulins with a yield of more than 4.5 g of immunoglobulins per liter of blood plasma applied to be obtained.

21 Claims, No Drawings

(56) References Cited

OTHER PUBLICATIONS

Radosevich et al., "Intravenous immunoglobulin G: trends in production methods, quality control and quality assurance," Vox Sanguinis, S. Karger AG, Basel, CH, vol. 98, No. 1, Jan. 1, 2010, pp. 12-28.
Noel and Morelli, 2nd Generation Expanded Bed Adsorption (EBA) Technology for the High Throughput Processing of Cohn Fraction Inter mediates, The Fifth Plasma Product Biotechnology Meeting (PPB07), May 2007, accessed at http://www.bo-conf.com/ppb07/present/papers/503.pdf.
English Translation of First Japanese Office Action issued in application No. 2014-519532.
English Translation of Second Japanese Office Action dated Nov. 7, 2016 issued in application No. 2014-519532.
English Translation of Taiwanese Office Action issued in application No. 101124715.
Australian Examination Report No. 1 issued in application No. 2012282566 dated Dec. 22, 2016.
Global Dossier family report for U.S. Pat. No. 7,186,410 (retrieved online on Jul. 12, 2016).

\* cited by examiner

METHOD FOR PREPARING A CONCENTRATE OF POLYVALENT IMMUNOGLOBULIN

The present invention relates to a method for preparing a concentrate of polyvalent immunoglobulins with view to therapeutical use.

Immunoglobulins (Ig) are synthesized by B lymphocytes and plasmocytes, which are distributed in the plasma, extravascular liquids and secretions. They are divided into 5 categories, isotypes or classes, on the basis of their protein structure: IgG, IgA, IgM, IgE and IgD. Their natural distribution in the human body is the following: IgG: 75%, IgA: 20%, IgM: 5% and <1% for IgE and IgD. Normally, there are from 8 to 15 g of IgG per liter of plasma. In the plasma, the half-life of circulating immunoglobulins of class IgG is of about 21 days, that of IgA, IgM, IgD, IgE is less than 7 days.

Polyvalent immunoglobulins of human origin and used pharmaceutically consist of 97% IgG corresponding to the presence of a large diversity of antibodies against various infectious agents.

The use of human plasma fractions enriched with polyvalent immunoglobulins for treating various congenital infections or deficiencies is known for its therapeutic effects. Polyvalent or normal immunoglobulins are administered in order to correct a primary immunodeficiency and certain secondary deficiencies (leukemias, myelomas or recurrent infections). They are to be disassociated from specific antibodies (anti-Rhesus or anti-D cytotoxic antibodies). They may be prescribed at very high dosages, up to 2 g/kg/day, in order to slow down the development of certain diseases, for which the physiopathology is poorly known, but includes a component of the immune type. Administration of polyvalent immunoglobulins has shown its at least transient efficiency in the treatment of thrombocytopenia of immunologic origin, also called idiopathic thrombocytopenic purpura. Polyvalent immunoglobulins may also have a beneficial effect in the treatment of Guillain-Barre's syndrome, demyelinating polyneuropathy, multiple sclerosis, myasthenic Lambert-Eaton's syndrome, dermatomyositis.

Polyvalent immunoglobulins contain various molecules so their mechanism of action is complex: by intervening at several levels, they modify the immune system balance of the patient and may thus have a beneficial effect.

Several methods for preparing concentrates of polyvalent immunoglobulins are already known to one skilled in the art. The best known preparation method comprises several steps with precipitation in ethanol (Cohn et al. 1946, J. Am. Chem. Soc. 68, 459).

Patent EP 0703 922 (Laboratoire Français du Fractionnement et des Biotechnologies, "Concentré d'immunoglobulines G à usage thérapeutique et procédé de production dudit concentré" (Immunoglobulin G concentrate for therapeutic use and method for producing said concentrate)) in particular describes a method for producing a concentrate of immunoglobulins G from human plasma or from cryoprecipitated plasma supernatant. This method does not comprise precipitation from ethanol and comprises a succession of chromatography steps and a step for viral inactivation by solvent/detergent. This method only allows a relatively low yield, because of the succession of chromatography steps, the described method actually including two anionic and cationic exchanger cycles in tandem as well as two ultrafiltration steps.

Patent EP 1 385 886 (Laboratoire Français du Fractionnement et des Biotechnologies, "Procédé de prépreparation de concentrés d'immunoglobulines humaines à usage thérapeutique" (Method for preparing human immunoglobulin concentrates for therapeutic use)) describes a method for preparing concentrates of human immunoglobulins comprising pre-purification by precipitation of lipid and protein contaminants and a single chromatography step carried out on an anion exchanger with an alkaline pH. With this method it is possible to obtain up to 4 g of immunoglobulins per liter of initially treated plasma.

The publication of Tanaka K. et al., 2000 ("High quality human immunoglobulin G purified from Cohn fractions by liquid chromatography" Braz J Med Bio Res 2000, 33(1): 27-30) describes a method for purifying immunoglobulins G from « I+II+II+», and « II+III» fractions obtained according to Cohn's method, by chromatographic separation on three types of gels, two ion exchange gels (Q-Sepharose FF and CM-Sepharose FF) and a filtration gel (Sephacryl S-300 HR). With this method it is possible to obtain up to 4.3±0.2 g of immunoglobulins G per liter of plasma.

Nevertheless, as the therapeutic indications of immunoglobulins have been multiplied, there exists a significant need for increasing the yield of the production of immunoglobulins, while making sure that the final product has high purity and is free of viral contaminants.

Therefore, the object of the present invention is a method for preparing a concentrate of human polyvalent immunoglobulins with a higher yield as compared with that of the methods known to one skilled in the art.

The invention thus relates to a method for preparing a concentrate of human polyvalent immunoglobulins from an initial solution of blood plasma or of a plasma fraction enriched with immunoglobulins, characterized in that it comprises:
(a) a step for removing protein contaminants with caprylic acid in order to obtain a solution free of proteases,
(b) a fluidized bed chromatography step for the solution free of proteases, said method allowing a concentrate of human polyvalent immunoglobulins with a yield of more than 4.5 g of immunoglobulins/liter of initial solution of blood plasma or of plasma fraction enriched with immunoglobulins to be obtained.

The solution obtained at the end of step (a) for removing protein contaminants with caprylic acid of the method of the invention has a protease concentration which complies with standard 2.6.15 of European Pharmacopeia 7.5 Edition 01/2012:0918, which is at most 35 IU/mL calculated relatively to a dilution of the preparation to be examined containing 30 g/L of immunoglobulins.

The invention is based on the observation that the combination of a step for removing protein contaminants with caprylic acid, with a fluidized bed chromatography step allows a surprising increase in the yield of the production of immunoglobulins.

In an embodiment, the invention comprises the combination of a carefully performed step for removing protein contaminants with caprylic acid at an acid pH followed by clarification at an acid pH of the supernatant obtained at the end of the treatment step with caprylic acid allowing immunoglobulins to be bound to a chromatography gel applied in a fluidized column (a gel of the anion exchange type and/or of the affinity type and/or of the « pseudo-affinity» type, preferably of the « mixed-mode» type), which allows an increase in the yield of the production of polyvalent immunoglobulins. Preferentially, the productivity may be increased if the conditions for eluting the polyvalent immunoglobulins from the chromatography gel allow direct compatibility with the following steps of the process without any formulation step by techniques of the dialysis or ultrafiltration type. In particular, the method according to the invention gives the possibility of obtaining a productivity gain of 0.25% of polyvalent immunoglobulins per liter of plasma and a final product having high purity (99%).

In a particular embodiment, the method of the invention comprises between the step for removing protein contaminants with caprylic acid (a) and the fluidized bed chromatography step (b), a step for clarification at an acid pH, preferably by depth filtration.

The elution steps will be advantageously defined in order to selectively extract immunoglobulins of the G type (IgG).

The invention also relates to a method for preparing a concentrate of human polyvalent immunoglobulins from an initial solution of blood plasma or of a plasma fraction enriched with immunoglobulins, characterized in that it comprises:
    (a) a step for removing protein contaminants with caprylic acid at an acid pH in order to obtain a solution free of proteases,
    (b) a clarification step at an acid pH,
    (c) a fluidized bed chromatography step for the solution free of proteases,
    (d) elution in a buffer for elution of immunoglobulins.

In particular, step (b) for clarification at an acid pH is carried out by depth filtration based on a porosity as high as possible but allowing the clarified supernatant to pass over a fluidized bed column.

The solution obtained at the end of step (a) for removing protein contaminants with caprylic acid of the method of the invention has a protease concentration which complies with the standard 2.6.15 of European Pharmacopeia 7.5 Edition 01/2012:0918, which is at most 35 IU/mL calculated relatively to a dilution of the preparation to be examined containing 30 g/L of immunoglobulins.

The invention also relates to the method as described above and integrating after step (b) for clarification at an acid pH, a step for raising the pH, corresponding to the conditioning of the polyvalent immunoglobulins allowing binding of the latter onto a chromatography gel applied in a fluidized mode.

Surprisingly, the concentrate of human polyvalent immunoglobulins obtained at the end of the method of the invention has an anti-complementary activity of less than 30%, which is determined with reference to the method indicated in European Pharmacopeia 7.5, edition 01/2012: 0918, paragraph 2.6.17.

By « polyvalent immunoglobulins » are meant within the scope of the invention, entire immunoglobulins, or fragments of immunoglobulins, such as F(ab')2 or F(ab) and any intermediate fraction obtained during the production process.

By « plasma fraction » is meant any blood solution obtained after a treatment which allows separation or fractionation of natural human blood plasma, notably any intermediate fraction obtained during the method for preparing a concentrate of polyvalent immunoglobulins.

By « plasma fraction enriched with immunoglobulins » is meant a plasma fraction containing a level of immunoglobulins above the one contained in natural human plasma.

By « I+II+III » or « II+III » precipitate, is meant a precipitate obtained from blood plasma fractionated with ethanol according to Cohn's method (Cohn et al. 1946, J. Am. Chem. Soc. 68, 459) or the method of Kistler and Nitschmann (1962, Vox Sang. 7, 14).

By « protein contaminants » are meant all proteins other than immunoglobulins of type G, for example and in a non-limiting way, immunoglobulins of type A, E or M as well as other plasma proteins such as, in a non-limiting way:
    albumin, transferrin, α2-macroglobulin, plasminogen, fibrinogen, etc.,
    coagulation factors such as in a non-limiting way, FX, FXI, or FXII,
    proteases such as, in a non-limiting way, kallikrein, prekallikrein, or the activator of prekallikrein, and
    anti-A and anti-B hemagglutinins.

By « fluidized bed chromatography » is meant a technique which by applying a flow in the reverse direction of gravity on chromatography beads with high density allows a space to be made between the latter thereby allowing a slightly clarified solution to pass into the chromatography column without causing any clogging of the solution flow. Fluidized bed chromatographies may be chromatographies of the ion exchange type, of the affinity type, of the « pseudo-afinity » type, or of the « mixed-mode » type (i.e. both with ion exchange and pseudo-affinity).

In particular, fluidized bed chromatography is achieved with the UpFront WIG gel of the « mixed-mode » type comprising the presence on the beads of a chemical ligand combining electrostatic charges and hydrophobic groups imparting specific pseudo-affinity for immunoglobulins.

Concentration of the caprylic acid used in the method according to the invention is performed with care, i.e. the precipitation of the contaminants is achieved with a sufficiently low final concentration of caprylic acid so as not to trap polyvalent immunoglobulins during precipitation of the other constituents of the solution. The caprylic acid concentration advantageously ranges from 0.5 to 1.5%, advantageously from 0.8 to 1.2%, in particular from 0.9 to 1.1% and most particularly is equal to 1% (the caprylic acid percentage corresponds to grams of caprylic acid per volume of solution to be treated).

In an embodiment, the step for removing protein contaminants with caprylic acid is carried out at a pH comprised between 4.3 and 4.9, preferably comprised between 4.6 and 4.8.

The applicant surprisingly noticed that the concentration of caprylic acid applied in the method for preparing a concentrate of polyvalent immunoglobulins according to the invention has a direct influence on the yield of the method when the latter comprises a subsequent clarification step. If the caprylic acid concentration is too low, precipitation will not be perfect, (in particular a significant portion of lipids remains in the solution) and the optional clarification step will be very difficult to apply. On the other hand, if the caprylic acid concentration is too strong, polyvalent immunoglobulins will be trapped in the formed precipitate and will no longer be available in the supernatant after optional clarification.

In an embodiment, a clarification step at an acid pH is added between the step for removing protein contaminants with caprylic acid and the fluidized bed chromatography step. This clarification step at an acid pH is carried out at a pH value comprised between 4.3 and 4.9, preferably between 4.4 and 4.8 and preferably at a pH comprised between 4.6 and 4.8.

In a particular embodiment, the clarification step at an acid pH is a step for clarification by depth filtration. This clarification is carried out so as to only retain the larger particles which may interfere with the operation of the fluidized bed. Preferably, filters having a rated retention rate from 15 to 100 µm, preferably from 25 to 70 µm or from 15 to 40 µm, are used. In an embodiment, the clarification filters of type SEITZ T5500 having a rated retention rate of 25-70 µm are used in this step and more particularly the filter T2600 for which the rated retention rate is 15-40 µm. Any type of filter, either charged or not, allowing equivalent clarification may be used. Clarification is advantageously achieved in the presence of filtration earths, thereby allowing a reduction in the filter surface to be used. In order to increase fluidity of the solution to be filtered, clarification is advantageously achieved between 4 and 30° C., more particularly between 10 and 25° C., for example between 20 and 25° C. Advantageously, the filter used in the clarification step according to the invention has a capacity of at least 40 liters per $m^2$ i.e. 8 kg of precipitate per $m^2$, more specifically 55 liters per $m^2$ i.e. 11 kg of precipitate per $m^2$.

At the end of depth filtration, the pH and the osmolality of the filtration supernatant are advantageously adjusted without any dialysis or ultrafiltration step, depending on the needs of the next step of the method.

In a particular embodiment, the fluidized bed chromatography step may be a chromatography of the « mixed-mode » type which comprises:

loading on a chromatography column equilibrated beforehand with a buffer at a pH comprised between 4.5 and 8, more particularly between 4.5 and 7.5; 4.5 and 7.0; 4.5 and 6.8; 4.5 and 6.5; 5.0 and 7.0; 5.0 and 6.5; 5.5 and 6.3; or between 5.7 and 6.3; of the solution having been subject to the clarification step by depth filtration adjusted beforehand to the same pH, i.e. a pH comprised between 4.5 and 8, more particularly between 4.5 and 7.5; 4.5 and 7.0; 4.5 and 6.8; 4.5 and 6.5; 5.0 and 7.0; 5.0 and 6.5; 5.5 and 6.3; or between 5.7 and 6.3, washing the aforesaid column with a buffered solution until all the non-adsorbed proteins on the column are removed, eluting the polyvalent immunoglobulins adsorbed on the column with an elution buffer adjusted to a pH comprised between 8 and 10, preferably between 8 and 9.8; 8.3 and 9.8; 8.5 and 9.8; 8.8 and 9.8; 9.0 and 9.8; 9.5 and 9.8, and recovering the solution enriched with human polyvalent immunoglobulins.

The chromatography of the « mixed-mode» type on a fluidized bed applied in the invention preferably uses beads having different sizes, which allows stabilization of the chromatography bed. The beads applied in the chromatography of the « mixed-mode» type on a fluidized bed according to the invention have an average density from 2.5 to 3.5 kg/L, a diameter comprised between 20 and 400 µm and a binding capability of polyvalent immunoglobulins under the conditions of the invention, which may advantageously exceed 70 g/L.

The elution applied in fluidized bed chromatography is for example an elution at a basic pH and at a low ionic force in order to be able to directly move on with the next step of the method, after having proceeded with simple pH and conductivity adjustments. An elution buffer which may be used within the scope of the invention may for example contain: glycine from 5 to 500 mM, notably 20 mM, and NaCl from 5 to 500 mM, notably 20 mM, at a pH comprised between 7 and 10, notably comprised between 9 and 10, notably comprised between 9.5 and 10, and more interestingly between a pH of 9.5 and 9.8.

In the case when the step following fluidized bed chromatography is not compatible with high ionic force conditions, and would accordingly require beforehand significant dilution or dialysis of the eluate obtained at the end of the fluidized bed chromatography step, an elution buffer having a high pH but a low ionic force may be used. An elution buffer which may be used within the scope of the invention may for example contain: glycine from 5 to 20 mM, notably 10 mM, at a pH comprised between 9.5 and 10.5, notably comprised between 9.8 and 10.5 and more interestingly between a pH of 9.8 and 10.2.

In a particular embodiment, the method according to the invention further comprises, after the fluidized bed chromatography step, one or more of the following steps:

(i) a viral inactivation step;

(ii) a chromatography step for exchanging anions of the solution obtained at the end of the preceding step with the purpose of removing the chemical components used during the viral inactivation step and of reducing IgA and IgM contamination;

(iii) a step for removing anti-A and anti-B antibodies from the solution obtained at the end of the preceding step;

(iv) a step for filtration through nanometric filters with decreasing porosity from 100 to 15 nm;

(v) a concentration step by ultrafiltration of the solution from the preceding step associated with a formulation step;

(vi) a conventional sterilizing filtration step.

The concentrate of polyvalent immunoglobulins obtained according to the method of the invention has generally been at least subject to a step for removing or inactivating at least one infectious agent. Among infectious agents, mention may be made of viruses and NCTAs (non-conventional transmissible agents) such as prions. Viral inactivation often comprises a treatment with chemicals, for example with a solvent and/or detergent and/or with heat, for example with UVC, gamma irradiation, and/or pasteurization. Nanofiltration is also helpful for removing infectious agents, notably viruses. Preferably, the method comprises at least one treatment with a solvent and detergent, and nanofiltration. The treatment with a solvent and/or detergent (generally called a solvent/detergent treatment) notably comprises treatment with tri-n-butyl phosphate (TnBP) and/or a detergent which is selected from Triton X-100, Tween (preferably Tween 80), sodium cholate and 2-[4-(2,4,4-trimethylpentan-2-yl)phenoxy]ethanol (Octoxinol). Nanofiltration generally refers to the filtration of the concentrate of polyvalent immunoglobulins through a filter with a pore size of less than 80 nm. Available filters are for example the BioEx, Planova™ 75 nm, Planova™ 35 nm, Planova™ 20 nm or Planova™ 15 nm (Asahi corporation), Ultipor DV 50 or DV 20 (Pall corporation), Virosart CPV (Sartorius), Viresolve NFR or NFP (Millipore) filters. Preferably, nanofiltration is achieved before the step (v) for concentrating polyvalent immunoglobulins by ultrafiltration associated with a formulation step. In a particular embodiment, the purified concentrate of polyvalent immunoglobulins is filtered on a sequence of filters with pore sizes between 15 and 50 nm, for example 20 or 35 nm.

Anion exchange chromatography applied in the method according to the invention is carried out at an alkaline pH and at a low ionic force in order to allow binding of polyvalent immunoglobulins. This step is carried out for example according to the method described in patent EP 1 385 886 (Laboratoire Français du Fractionnement et des Biotechnologies, "Procédé de préparation de concentrés d'immunoglobulines humaines á usage thérapeutique" (Method for preparing human immunoglobulin concentrates for therapeutic use)). The resin is equilibrated with any buffer having buffering power at low concentration for a pH comprised between 8.5 and 9.5, such as Tris buffers or more particularly glycine buffers. The glycine concentration may be comprised between 5 and 50 mM, for example between 5 and 20 mM and more particularly between 8 and 10 mM. The pH will be adjusted between 8.5 and 9.5 and more particularly between 8.9 and 9.1.

Advantageously, the eluate from fluidized bed chromatography is diluted and adjusted in pH so as to allow binding of polyvalent immunoglobulins onto the anion exchange chromatographic support. This dilution is carried out with water so as to bring conductivity under a value of 1,500 µS/cm and more preferably under 1,100 µS/cm. The column is washed in the equilibration buffer, and the polyvalent immunoglobulins are then eluted in a 20 mM Na/Na$_2$ PO$_4$ buffer, at a pH of 6.2. Finally, the column is washed with a 150 mM NaCl solution.

Removal of the anti-A and anti-B antibodies in the solution obtained from anion exchange chromatography may be carried out according to the method described in patent application WO 2007/077365 (Laboratoire Français du Fractionnement et des Biotechnologies, "Immunoglobulin G (IgG) concentrate depleted of anti-A and anti-B antibodies and of polyreactive IgGs"). The solution obtained in the previous step is subject to a step for removing anti-A and anti-B antibodies by immunoaffinity chromatography by percolation of said concentrate of polyvalent immunoglobulins on a mixture of supports, the matrices of which are grafted with oligosaccharide groups antigenically similar to the A and B blood groups.

In a particular embodiment of the invention, the initial solution is blood plasma or a plasma fraction enriched with immunoglobulins by methods well-known to one skilled in the art, and notably by fractionation with ethanol and/or by chromatographic separation.

In a particular embodiment, the initial solution is a «I+II+III» precipitate or a «II+III» precipitate obtained from blood plasma fractionated with ethanol according to the Cohn or Kistler and Nitschmann method (1962, Vox Sang. 7, 414), and put back into solution. Advantageously, the «I+II+III» precipitate or the «II+III» precipitate is put back into solution within the scope of the invention in purified water for injections (wfi) or in a solution containing ions. The solution containing ions used within the scope of the invention may be a solution comprising NaCl at a concentration of less than or equal to 20 mM, preferably comprised between 5 and 15 mM, and preferably equal to 10 mM.

In another embodiment, putting back the «I+II+III» precipitate or the «II+III» precipitate into solution is achieved under conditions allowing precipitation of the contaminating fibrinogen. Precipitation of contaminating fibrinogen may then be obtained by treating the «I+II+III» precipitate or the «II+III» precipitate with a precipitation solution specific of fibrinogen, as for example with a solution of CaCl$_2$, the concentration of which is less than or equal to 20 mM, preferably comprised between 5 and 15 mM, and preferably with a 10 mM solution of salts. In such an embodiment, the fibrinogen remains under precipitated form, whereas polyvalent immunoglobulins are resolubilized.

A particular embodiment of the invention relates to a method for preparing a concentrate of human polyvalent immunoglobulins, comprising:
  (i) a step for removing protein contaminants with caprylic acid;
  (ii) a clarification step by depth filtration;
  (iii) a fluidized bed chromatography step of the «mixed-mode» type;
  (iv) a viral inactivation step by a solvent/detergent treatment;
  (v) a anion exchange chromatography step;
  (vi) a step for removing anti-A and anti-B antibodies;
  (vii) filtration through nanometric filters with decreasing porosity from 100 to 15 nm;
  (viii) a step for concentration by ultrafiltration of the solution from the previous step associated with a formulation step, and then a conventional sterilizing filtration step.

In a more particular embodiment, the invention relates to a method for preparing a concentrate of human polyvalent immunoglobulins, comprising:
  (i) treatment of an initial solution of blood plasma or of a plasma fraction enriched with immunoglobulins by fractionation with ethanol, in order to obtain «I+II+III» or «II+III» precipitate according to Cohn's method (already cited) or the method of Kistler and Nitschmann (1962, Vox Sang. 7, 414);
  (ii) putting back the «I+II+III» or «II+III» precipitate into solution with wfi water, with stirring, at 20° C. (preferentially 4 to 15° C.). Various ions may be provided in order to facilitate the putting back of the precipitated polyvalent immunoglobulins into solution, for example cations such as Na$^+$, anions such as Cl$^-$, for example NaCl. The concentration of the salt is less than or equal to 20 mM, preferably comprised between 5 and 15 mM, and preferably equal to 10 mM, such as for example NaCl at a molarity of 10 mM;
  (iii) precipitation from the «I+II+III» or «II+III» precipitate put back into solution, of protein contaminants with caprylic acid at a concentration from 0.5 to 1.5%, notably from 0.8 to 1.2%, particularly from 0.9 to 1.1%, in order to obtain a plasma solution free of proteases, and then adjustment of the pH between 4.3 and 4.9, preferably between 4.4 and 4.8, and preferably between 4.6 and 4.8. In an embodiment, adjustment of the pH is carried out with HCl;
  (iv) filtration of the plasma solution free of proteases stemming from step (iii) at an acid pH with a depth filter having the largest porosity possible allowing injection of the filtrate onto a chromatography column used in a fluidized bed mode;
  (v) adjustment of the pH and of the osmolality of the solution from step (iv),
  (vi) fluidized bed chromatography of the solution obtained at the end of the previous step, in order to obtain a blood solution enriched with human polyvalent immunoglobulins. Advantageously, said chromatography should allow elution of the polyvalent immunoglobulins in a buffer close to the buffer required for the next steps of the method, in order to limit the losses of polyvalent immunoglobulins which may be due to dialysis, ultrafiltration step or any step required for reformulating the solution;
  (vii) treatment with a solvent/detergent notably comprising treatment with tri-n-butylphosphate (TnBP) and/or a detergent which is selected from Triton X-100, Tween (preferably Tween 80), sodium cholate and 2-[4-(2,4,4-trimethylpentan-2-yl)phenoxy]ethanol (Octoxinol), for inactivating viruses in the solution obtained at the end of the previous step;
  (viii) anion exchange chromatography of the solution obtained at the end of the previous step, using a cross-linked polysaccharide or vinyl polymer gel, grafted with TMAE groups in order to remove the solvents and detergents used in the preceding step and for removing contaminants of the IgA and IgM type;

(ix) affinity chromatography as described in patent application WO 2007/077365 (Laboratoire Français du Fractionnement et des Biotechnologies, "Immunoglobulin G (IgG) concentrate depleted of anti-A and anti-B antibodies and of polyreactive IgGs".) in order to remove the anti-A and anti-B antibodies from the solution obtained at the end of the preceding step;

(x) nanofiltration of the solution obtained at the end of the preceding step, by using a pre-filter with 50 nm porosity (for example on a PALL DV20 filter) or 35 nm porosity (for example on a PLANOVA 35 N filter), followed by a filter with porosity of 20 nm (for example a PLANOVA 20 N filter) or 15 nm (for example a PLANOVA 20 N or BIOEX filter) in order to remove prions or viruses resistant to the treatment of step (ix);

(xi) concentration or diafiltration of the solution obtained at the end of the preceding step, in order to obtain a solution containing at least 50 g/L of polyvalent immunoglobulins.

The solution obtained at the end of the step (iii) for removing contaminants with caprylic acid of the method of the invention has a protease concentration which complies with the standard 2.6.15 of European Pharmacopeia 6.7, Edition 01/2012:0918, which is at most 35 IU/mL calculated relatively to a dilution of the preparation to be examined containing 30 g/L of immunoglobulins.

The object of the invention is also a concentrate of human polyvalent immunoglobulins obtained by the method of the invention characterized in that said concentrate has an anti-complementary activity of less than 30%.

The object of the invention is also a method for preparing a pharmaceutical composition of liquid, frozen or freeze-dried human polyvalent immunoglobulins, characterized in that:

a. adding to the concentrate of human polyvalent immunoglobulins obtained according to the method described in the invention, one or several pharmaceutically acceptable stabilizers, and b. optionally, freezing or freeze-drying the pharmaceutical preparation obtained in the preceding step;

so that said pharmaceutical preparation is in a liquid, frozen or freeze-dried form.

Pharmaceutically acceptable stabilizers used within the scope of the invention are for example those described in patent applications FR 2 853 551, FR 2 961 107 and FR 2 962 650. The application FR 2 853 551 describes a stabilizing formulation comprising an alcohol sugar such as mannitol, glycine and a non-ionic detergent. The mannitol concentration is advantageously comprised between 30 g/L and 50 g/L, that of glycine between 7 g/L and 10 g/L and that of non-ionic detergent between 20 and 50 ppm. Application FR 2 961 107 describes a stabilizing formulation comprising glycine and a non-ionic detergent at a pH of less than or equal to 4.8. The glycine concentration is at least 200 mM, preferably 250 mM±50 mM and that of the non-ionic detergent is comprised between 20 and 100 mg/L, preferably 35 mg/L±15 mg/L, still preferably 50 mg/L. Application FR 2 962 650 describes the addition to a preparation of human immunoglobulins G, of excipients selected from amino acids, sugars, derivatives of sugars, salts and surfactants, said surfactants being added at a concentration below the critical micellar concentration of said surfactants.

The object of the invention is also the use of a liquid, frozen or freeze-dried pharmaceutical composition of human polyvalent immunoglobulins, in particular a liquid, frozen or freeze-dried pharmaceutical composition of human polyvalent immunoglobulins obtained according to the method of the invention, for treating pathologies, such as demyelinating polyneuropathies, multiple sclerosis, myasthenic Lambert-Eaton syndrome, dermatomyositis, for substitutive treatment in the case of primary immunodeficiencies such as congenital agammaglobulinemias, and congenital hypogammaglobulinemias, variable common immunodeficiency, severe combined immunodeficiency, Wiskott Aldrich syndrome, myeloma or chronic lymphoid leukemia with severe secondary hypogammaglobulinemia and recurrent infections, recurrent infections in HIV-infected children, or for the treatment of primary immunodeficiencies with hypogammaglobulinemia or functional impairment of humoral immunity. The present invention also comprises the use of the liquid, frozen or freeze-dried pharmaceutical composition of human polyvalent immunoglobulins of the invention for treating secondary immunodeficiencies of humoral immunity, in particular chronic lymphoid leukemia or myeloma with hypogammaglobulinemia or associated with recurrent infections, allografting of hematopoietic strain cells with hypogammaglobulinemia associated with an infection, as well as immunomodulating treatment of idiopathic thrombocytopenic purpura (ITP) in adults and children in the case of significant hemorrhagic risk or before a medical or surgical operation for correcting the platelet level, of Birdshot retinochorioditis, of Guillain-Barré syndrome, of multifocal motor neuropathy (MMN), chronic inflammatory demyelinating polyneuropathy (CIDP), and Kawasaki's disease.

The following examples describe embodiments of the method according to the invention. The examples below aim at clarifying the object of the invention and illustrating advantageous embodiments, but by no means aim at restricting the scope of the invention.

EXAMPLES

Examples 1

1.1 Putting the «I+II+III» Precipitate Back into Solution

As a starting material the «I+II+III» precipitate is used, the one obtained from blood plasma fractionated with ethanol according to the Cohn or Kistler and Nitschmann method (1962, Vox Sang. 7, 414). This precipitate is put back into solution in an amount of 56.7 g for 228 mL of demineralized water or equivalent proportions. The mixture is stirred for 20 minutes at 15° C.±5° C. The temperature is then raised to 22° C.±2° C. and caprylic acid (1% weight/volume) is slowly added into the «I+II+III» precipitate put back into solution. The pH of the obtained solution after adding caprylic acid is adjusted to 4.8 and the solution remains with stirring for 60 minutes.

1.2 Depth Filtration

The resulting solution is clarified by depth filtration on a SEITZ® T 2600 filter (Pall Corporation). This filtration retains both the filtration adjuvants present in the «I+II+III» precipitate and the protein precipitate generated by the addition of caprylic acid.

The pH of the sample is also advantageously studied in order to optimize the filtration yield.

The pH of the protein solution is adjusted to 6.0 only after filtration. Indeed, the adjustment of the pH from 4.8 to 6.0 generates a slight precipitate (insolubility of polyvalent immunoglobulins) retained by the filter and therefore a reduction in the filtration yield of polyvalent immunoglobulins.

The rinsing volume of the filter (apyrogenous purified water) is equivalent to the volume of the initial sample in order to optimize the final yield.

1.3 Chromatography of the «Mixed-mode» Type on a Fluidized Bed

The operating conditions are the following:
Equilibration and washing buffer: 20 mM Na/Na$_2$PO$_4$ at pH 6.
Elution buffer: 20 mM glycine/20 mM NaCl at pH 9.8. By selecting elution by a pH effect in a Gly/NaCl buffer, it is possible by simple dilution (adjustment of the conductivity and pH) to obtain a sample ready to be injected onto the ion exchange column (TMAE Fractogel).

1.4 Treatment with Solvent/Detergent

The eluate from the chromatography of the «mixed-mode» type on a fluidized bed according to example 1.3 is subject to a viral inactivation treatment with solvent/detergent as described by Neurath and Horowitz (U.S. Pat. No. 4,764,369).

The 10 times concentrated solvent/detergent mixture contains 3% of TnBP (tri(n-butyl)phosphate) and 10% of Octoxinol. The final concentration in the eluate is 0.3% of TnBP and 1% of Octoxinol.

After 1 hour of inactivation, the eluate is adjusted to pH 9.0 and diluted in water in order to obtain a conductivity of less than 1,100 µS/cm.

1.5 Ion Exchange Chromatography

The ion exchange gel applied is TMAE-Fractogel®, Merck.

Pre-equilibration buffer: glycine 80 mM/NaCl 80 mM at pH 9.
Equilibration buffer: glycine 9 mM/NaCl 9 mM at pH 9.

After loading the sample, the column is washed with the equilibration buffer and it is then eluted in a 20 mM Na/Na$_2$PO$_4$ buffer at pH 6.2.

1.6 Affinity Chromatography

The applied affinity gel is Iso A/Iso B Hypercel, Pall Corporation.

The eluate of TMAE chromatography is subject to this affinity chromatography, in order to remove the anti-A and anti-B antibodies. The polyvalent immunoglobulins of interest cross the column without being retained.

Equilibration of the gel with demineralized water
Recovery of the non-adsorbed fraction without washing the column.

1.7 Filtration

The protein solution from the affinity chromatography is filtered on a depth filter 90LA CUNO, 3M and then on a 0.2 µm filter. The filters are rinsed with water and the rinsing solution is incorporated to the filtrate.

1.8 Nanofiltration

The preceding filtrate, adjusted to pH 4.5 is pre-filtered on line on a Fluorodyne II filter 0.1 µm, Pall Corporation and nanofiltered on a DV50 filter, Pall Corporation, and then on a Planova 20N filter from Asahi.

1.9 Formulation

The product is pre-concentrated to about 80 g/L by ultrafiltration on a cassette with a cut-off threshold of 30 kDa, and then diafiltered at constant volume until the conductivity is <600 µS/cm. The product is then formulated and adjusted to 50 g/L of proteins.

Example 2

Obtaining a Concentrate of Polyvalent Immunoglobulins by Applying the Method of the Invention on a Pilot Scale 2.1 Putting Back the «I+II+III» Precipitate Back into Solution The precipitate «I+II+III» is used as a starting material, obtained from blood plasma fractionated with ethanol according to the Kistler and Nitschmann method (1962, Vox Sang. 7, 414). This precipitate is put back into solution in an amount of 3 kg for 12 L of demineralized water. The mixture is stirred for 20 minutes at least at 10° C.±3° C. Next, the temperature is raised to 22° C.±2° C. and caprylic acid (1% weight/volume) is slowly added into the «I+II+III» precipitate put back into solution. The pH of the obtained solution after addition of caprylic acid is adjusted to 4.8 and the solution remains with stirring for 60 minutes.

2.2 Depth Filtration

The resulting solution is clarified by depth filtration on a SEITZ® T 2600 (Pall Corporation) filter. This filtration retains both the filtration adjuvants present in the «I+II+III» precipitate and the protein precipitate generated by addition of caprylic acid. For this test, the surface area used is 8.7 kg of precipitate/m$^2$ of filtering medium.

The rinsing volume of the filter (apyrogenous purified water) is equivalent to the volume of the initial sample i.e. 15 L.

2.3 Chromatography of the «Mixed-mode» Type on a Fluidized Bed

The chromatography gel applied is Rhobust IGIV gel, Upfront.

4.3 L of gel in a column with a diameter of 10 cm.

The operating conditions are the following:
Equilibration and washing buffer: 20 mM Na/Na$_2$PO$_4$ at pH 6.
Elution buffer: 20 mM glycine/20 mM NaCl at pH 9.8.

2.4 Treatment with Solvent/Detergent

The eluate from chromatography of the «mixed-mode» type on a fluidized bed undergoes a viral inactivation treatment with solvent/detergent as described by Neurath and Horowitz (U.S. Pat. No. 4,764,369).

The 10 times concentrated solvent/detergent mixture contains 3% of TnBP (tri-n-butylphosphate) and 10% of Octoxinol. The final concentration in the eluate is 0.3% of TnBP and 1% of Octoxinol.

After at least 1 hour of inactivation, the eluate is adjusted to pH 9.0 and diluted with water in order to obtain a conductivity of less than 1,100 µS/cm.

2.5 Ion Exchange Chromatography

The ion exchange gel applied is EMD-TMAE Fractogel®, Merck.

4 L of gel in a column with a diameter of 12.7 cm.
Pre-equilibration buffer: glycine 80 mM/NaCl 80 mM at pH 9.
Equilibration buffer: glycine 9 mM/NaCl 9 mM at pH 9.
After loading the sample, the column is washed in the equilibration buffer.
Next, it is eluated in a 20 mM Na/Na$_2$PO$_4$ buffer, at pH 6.2.

2.6 Affinity Chromatography

The affinity gel applied is Iso A/Iso B Hypercel, Pall Corporation.

154 mL of gel in a column with a diameter of 7 cm.

The eluate from TMAE chromatography is subject to this affinity chromatography, in order to remove the anti-A and anti-B antibodies. The polyvalent immunoglobulins of interest cross the column without being retained.

Equilibration of the gel in demineralized water
Recovery of the non-adsorbed fraction without washing the column.

2.7 Filtration

The protein solution from Iso A/Iso B Hypercel affinity chromatography is filtered on a depth filter 90LA CUNO, 3M, and then on a 0.2 μm filter. The rinsing of the filters in water is incorporated to the filtrate.

2.8 Nanofiltration

The preceding filtrate adjusted to pH 4.5 is pre-filtered on line on a Fluorodyne II 0.1 μm filter, Pall Corporation and nanofiltered on a DV50 filter, Pall Corporation, and then on a Planova 20N filter from Asahi.

2.9 Formulation

The product is pre-concentrated to about 80 g/L by ultrafiltration on a cassette with a cut-off threshold of 30 kDa, and then diafiltered at constant volume until the conductivity is less than <600 μS/cm. The product is then formulated and adjusted to 50 g/L of proteins.

Example 3

Yield of the Method

Three batches were made with three different « I+II+III» precipitates according to the method in accordance with the invention described in Example 1 and specified in Example 3. Removal of the proteases is obtained with 1% of caprylic acid. Filtration is carried out on a SEITZ T2600 plate filter-press.

A control batch is treated according to the reference method, as described in patent application EP 1 385 886.

The yield results of the novel method are shown in the table below:

| Accumulated yields in g/L of proteins or of plasma Ig at the formulated concentrated stage | | |
|---|---|---|
| | Batch according to the invention 10AXTO1064 015 (Batch 1) | Control batch treated according to the method as described in EP 1 385 886 10AXTO1064 038 |
| Yield in g of proteins per liter of treated plasma. | 5.22 | 4.67 |
| Yield in g of polyvalent Igs per liter of treated plasma | 4.75 | 4.49 |

The method according to the invention allows an increase in the yield in g of polyvalent immunoglobulins per liter of treated plasma, as compared with the reference method (EP 1 385 886).

The gain in the example above is 0.26 g of IgG/L of plasma, between the batch according to the invention and the control batch made from the same precipitate.

Example 4

Anti-complementary Activity

Three exploratory batches were made according to the method of the invention at a pilot scale from three different « I+II+III» precipitates. These batches were compared with a batch made on the same scale (pilot size), but according to the industrial method for producing immunoglobulins by intravenous injection as described in patent EP 1 385 886, and three industrial batches prepared according to the method described in application EP 1 385 886, made from the same precipitates.

A batch made with the pilot size corresponds to a batch for which the size represents at least 10% of the industrial batch.

The batches according to the invention have an anti-complementary activity (ACA) measured according to the test of European Pharmacopeia 7.5, edition 01/2012:0918, paragraph 2.6.17, always less than those of the batches made according to the method described in application EP 1 385 886. Moreover, the progression observed within 18 months on this criterion is less for the batches made according to the invention.

The anti-complementary activity (ACA) results are shown in the table below:

| | T = 0 | T = +18 months | Progression (%) |
|---|---|---|---|
| Exploratory batches made to the pilot size prepared according to the method of the invention: | ACA % | ACA % | |
| Batch 1* | 28 | 31 | 11% |
| Batch 2** | 27 | 31 | 15% |
| Batch 3*** | 27 | 31 | 15% |
| Batch made to the pilot size* prepared according to the method described in application EP 1 385 886: | 33 | 40 | 21% |
| Industrial batches made according to the method described in application EP 1 385 886: | | | |
| Industrial batch 1* | 36 | 38 | 6% |
| Industrial batch 2** | 32 | 39 | 22% |
| Industrial batch 3*** | 32 | 37 | 16% |

*, , *batches made with the same precipitates

The method of the invention therefore gives the possibility of obtaining a concentrate of polyvalent immunoglobulins for which the anti-complementary activity is less than 30%.

Example 5

Purity of Immunoglobulins Produced According to the Method of the Invention

The analytic purity data for the pilot batches described in Example 2 are summarized in the table below.

| Analysis | Measurement method | Pilot batch No. 1 | Pilot batch No. 2 | Pilot batch No. 3 | Average of the industrial batches obtained according to the method described in application EP 1 385 886 |
|---|---|---|---|---|---|
| pH | Ph. Eur (2.2.35) | 5.0 | 4.8 | 4.8 | 4.9 |
| Osmolality mosmol/kg | Ph. Eur (2.2.29) | 297 | 294 | 299 | 297 |

| Analysis | Measurement method | Pilot batch No. 1 | | Pilot batch No. 2 | | Pilot batch No. 3 | | Average of the industrial batches obtained according to the method described in application EP 1 385 886 | |
|---|---|---|---|---|---|---|---|---|---|
| DTM polymers (%) | Ph. Eur (2.2.29) | <0.4 | | <0.4 | | <0.4 | | 0.5 | |
| Dimers (%) | Ph. Eur (2.2.29) | 2.7 | | 3.7 | | 2.4 | | ND | |
| Monomers (%) | Ph. Eur (2.2.29) | 96.3 | | 95.3 | | 96.4 | | 98.7* | |
| Fragments (%) | Ph. Eur (2.2.29) | 1 | | 1.1 | | 1.1 | | 1 | |
| Total proteins (g/l) | Ph. Eur (2.5.33) | 51 | | 49 | | 49 | | 50 | |
| Protein level (%) | Ph. Eur (2.5.33) | 98 | | 98 | | 98 | | | |
| | | | % proteins | | % proteins | | % proteins | | % proteins |
| IgG g/L | Nephelometry** | 46.4 | 91 | 46 | 95 | 47.6 | 96 | 45.7 | 92 |
| IgG1 g/L | Nephelometry** | 29.5 | 58 | 27.1 | 56 | 26.7 | 54 | 28 | 56 |
| IgG2 g/L | Nephelometry** | 18 | 35 | 17.8 | 37 | 16.7 | 34 | 16.1 | 32 |
| IgG3 g/L | Nephelometry** | 1.4 | 3 | 1.2 | 2 | 1.3 | 3 | 1.1 | 2 |
| IgG4 g/L | Nephelometry** | 1.1 | 2 | 1 | 2 | 1 | 2 | 0.9 | 2 |
| IgA g/L | ELISA*** | 7.4 | 0.01 | 7.1 | 0.01 | 6 | 0.01 | 8.6 | 0.02 |
| IgE g/L | Nephelometry** | <0.8 | ND | <0.8 | ND | <0.8 | ND | <0.8 | ND |
| IgM g/L | Nephelometry** | 0.23 | | 0.2 | | 0.18 | | 0.16 | |
| Antibody anti-Hbs Ag (IU/mL) | ELISA*** | 5.1 | | 3.5 | | 3.3 | | 4.6 | |
| Albumin mg/L | Nephelometry** | <2.2 | | <2.2 | | <2.2 | | <2.2 | |
| Transferrin mg/L | Nephelometry** | <2.1 | | <2.1 | | <2.1 | | <2.1 | |
| Activator of prekallikrein | Ph. Eur (2.6.15) | <1 | | <1 | | <1 | | <2 | |
| Anti-A hemagglutinins | Ph. Eur (2.6.20) | 4 | | 16 | | 8 | | 8 | |
| Anti-B hemagglutinins | Ph. Eur (2.6.20) | 2 | | 4 | | 8 | | 4 | |
| Anti-complementary activity (%) | Ph. Eur (2.6.17) | 28 | | 27 | | 27 | | 33 | |

Ph. Eur: European Pharmacopeia 6$^{th}$ edition
*Monomers + dimers.
**Pressac M, Later R. "Dosages sériques d'IgG, IgA, IgM, transferrine et haptoglobine. II Précision analytique et comparaison des résultats fournis par différents analyseurs". Ann Biol Clin 1995; 53: 273-81.
***R. A. Goldsby, T. J. Kindt, B. A. Osborne et J. Kuby, "Enzyme-Linked Immunosorbent Assay" in Immunology, 5e édition, pages 148-150, W. H. Freeman, New York, 2003

The sum "monomers+dimers", the distribution of the sub-classes, the levels of contaminants and the anti-complementary activity are equivalent for the immunoglobulins from the method of the invention or from the reference method according to patent EP 1 385 886. These characteristics meet the criteria of the European Pharmacopeia.

Example 6

Stability of the Immunoglobulins Produced According to the Method of the Invention The formulated products from pilot batches described in Example 2 were kept at 4° C. and aliquots of the industrial batches were made with the same initial precipitates and kept at the same stage under the same conditions. Samplings carried out every six months gave the possibility of observing on three criteria the differences between the batches obtained according to the invention (pilot batches 1, 2 and 3) and the batches obtained according to the reference industrial method EP 1 385 886 (industrial batches 1, 2 and 3). The three measured criteria were the following:

measurement of the concentration of immunoglobulins G (IgG) and that of the concentration of anti-Hbs immunoglobulins according to the method described in European Pharmacopeia 6.7 (Pharmeuropa, volume 21, number 2, April 2009), paragraph 2.7.1, and determination of the molecular size (polymers, dimers, monomers and fragments) according to the method described in European Pharmacopeia 6.7 (Pharmeuropa, Volume 21, Number 2, April 2009), paragraph 2.2.29.

The table below accounts for these differences:

| Batches prepared according to the method of the invention: | IgG g/L | Ig αHbs IU/mL | DTM % (aggregates/dimers/monomers/fragments) | IgG g/L | Ig αHbs IU/mL | DTM % (aggregates dimers/monomers/fragments) |
|---|---|---|---|---|---|---|
| | | | T = 0 | | | T = +6 months |
| Pilot batch 1* | 46.4 | 5.1 | <0.4/2.7/96.3/1.0 | 43.7 | 5.2 | <0.4/5.7/93.4/<1.0 |
| Pilot batch 2** | 46.0 | 3.5 | <0.4/3.7/95.3/1.1 | 42.7 | 3.5 | <0.4/5.2/93.7/1.1 |
| Pilot batch 3*** | 47.6 | 3.3 | <0.4/2.4/96.4/1.1 | 43.5 | 3.0 | <0.4/4.3/94.6/1.0 |
| Batch made to the pilot size* prepared according to the method described in EP1385886: | 49.6 | 6.1 | <0.4/3.6/95.7/<1 | 45.3 | 5.4 | <0.4/5.1/93.9/<1.0 |
| Industrial batches prepared according to the method described in EP1385886: | | | | | | |
| Industrial batch 1* | 45.9 | 5.1 | 0.4/98.8/1.1 | 46.6 | 5.5 | <0.4/4.8/94.1/1.0 |
| Industrial batch 2** | 46.0 | 4.7 | 0.7/98.6/1.0 | 44.9 | 4.4 | 0.9/5.1/93.2/<1.0 |
| Industrial batch 3*** | 45.2 | 3.9 | 0.4/98.6/1.0 | 44.4 | 3.5 | <0.4/4.6/94.3/<1.0 |
| | | | T = +12 months | | | T = +18 months |
| Pilot batch 1* | 51.7 | 5.2 | <0.4/5.6/93.3/1.0 | 48.5 | 5.0 | <0.4/4.8/94.1/1.0 |
| Pilot batch 2** | 49.7 | 3.7 | <0.4/5.3/93.7/<1.0 | 45.7 | 3.3 | <0.4/4.4/94.5/1.1 |
| Pilot batch 3*** | 49.5 | 3.2 | <0.4/4.7/94.3/1.0 | 47.6 | 3.1 | <0.4/4.4/94.5/1.1 |
| Batch made to the pilot size* prepared according to the method described in EP1385886 | 51.8 | 5.7 | <0.4/5.4/93.6/<1.0 | 49.1 | 5.4 | <0.1/5.2/93.8/1.0 |
| Industrial batches prepared according to the method described in EP1385886: | | | | | | |
| Industrial batch 1* | 51.4 | 5.9 | <0.4/4.8/93.6/1.0 | 46.5 | 5.3 | <0.4/4.1/94.8/1.0 |
| Industrial batch 2** | 48.2 | 4.5 | 0.7/4.8/93.6/1.0 | 46.2 | 4.3 | 0.7/4.9/93.5/1.0 |
| Industrial batch 3*** | 49.5 | 3.7 | <0.4/4.4/94.4/1.0 | 47.1 | 3.4 | <0.4/4.4/94.4/1.0 |

*, , *batches made with the same precipitates.

Analysis of the data shows:
 stability of the IgG concentration over 18 months and homogeneity of the 7 batches,
 stability of the concentration of the anti-Hbs Igs over 18 months: each batch being specific to this criterion,
 a constant «monomers+dimers» sum greater than the 85% required by the pharmacopeia and this for each batch over 18 months.

Example 7

A Method Comprising a Step for Caprylic Precipitation, a Clarification Step and a Chromatography Step of the «Mixed Mode» Type on a Fluidized Bed The treatment with caprylic acid has the purpose of removing by precipitation (the immunoglobulins remaining in solution) part of the contaminating proteins from the plasma and most particularly proteases. Depending on the percentage of caprylic acid used and on the method for separating the supernatant and the precipitate, a more or less significant portion of the immunoglobulins may be lost. Experimental conditions were tested so as to have the most coarse clarification possible compatible with fluidized bed chromatography and generating the smallest loss of immunoglobulins. For this, filters with increasing porosity were compared without caprylic precipitation in a first phase, and then confirmed subsequently with treatment with caprylic acid at different concentrations.

Test on a filter with a diameter of 90 i.e. 50 cm$^2$ (with rinsing),
No precipitation with caprylic acid

| | Test number | | |
|---|---|---|---|
| | 440 077 | 440 078 | 440 079 |
| Filter type | Pall Supradur50P | Pall/Seitz T 5500 | Pall/Seitz T 2600 |
| Porosity | 4-8 μm | 25-70 μm | 15-40 μm |
| pH | 4.8 | 4.8 | 4.8 |
| Flow volume mL | 150 | 150 | 150 |
| Flow rinsing | 0 | 75 | 75 |
| Recovered volume mL | 9 (water) | 208 | 216 |
| Initial IgG g/L | 14.35 | 15.05 | 15.05 |
| Filtrate IgG g/L | ND* | 10.5 | 10.2 |
| Yield % | ND* | 97 | 98 |
| Volume/surface l/m$^2$ | ND* | 30 | 30 |

*clogging of the filter, no metering carried out.

These results show that a minimum porosity of the order of 10-20 μm has to be applied in order to limit the IgG loss because of clogging. The filter T2600 was selected relatively to the filter T5500 for its lower porosity at an equivalent IgG yield.

The percentage of added caprylic acid having an impact on the precipitation of the proteases and on the filterability of the solution, a range of caprylic acid from 0.5 to 1% without adding any filtration adjuvant was tested. The obtained results are compared with those resulting from control clarification by simple centrifugation.

| Test - Re-suspending (RES) 1% caprylic acid - filter with diameter 90 i.e. 50 cm², load 210 mL | | | | |
|---|---|---|---|---|
| | | | RES pH 4.8 (1) | Clarified RES (2) |
| Test A | 1% SEITZ 2600 filtration | IgG g/L | 13.7 | 9.7 |
| | | Yield (YLD) % | 100 | 76 (3) |
| | | Proteases mOD/mL | 570 | 13 |
| Test B | 0.5% SEITZ 2600 filtration | IgG g/L | 15 | 9.4 |
| | | YLD % | 100 | 51 (3) |
| | | Proteases mOD/mL | NR | NR |
| Test C | 0.5% centrifugation | IgG g/L | 14.1 | 12.4 |
| | | YLD % | 100 | 72 |
| | | Proteases mOD/mL | 967 | 250 |

(1) Precipitate put back into solution, adjusted to pH 4.8 before clarification.
(2) Precipitate put back into solution pH-adjusted and clarified.
(3) Rinsing of the filters with a volume corresponding to half of the product to be clarified.

The control by centrifugation shows that part of the immunoglobulins is lost in the precipitate, if the latter is not rinsed, this technique was not retained. The most interesting tested condition is the 1% concentration of caprylic acid: protease contamination is low and the immunoglobulin loss is less than 30%. A concentration of 1% of caprylic acid therefore appears to be the best compromise between filterability, yield and removal of the proteases.

In order to increase the yield, the test below was conducted with a smaller load (180 mL instead of 210 mL) and by increasing the washing volume of the precipitate with the rinsing buffer as described in the table below.

| Test 09AXTO440 126 - RES 1% caprylic acid - filter de diameter 90 i.e. 50 cm², load 180 mL. | | | | |
|---|---|---|---|---|
| Steps | Volume (mL) | IgG (g/L) | Amount (mg) | Yield (YLD) % |
| RES pH 4.8 | 210 | 13.65 | 2866.5 | 100 |
| RES filter | 180 | 11.2 | 2016.0 | 70.3 |
| Rinsing 1 | 30 | 3.71 | 111.3 | 3.9 |
| Rinsing 2 | 30 | 2.26 | 67.8 | 2.4 |
| Rinsing 3 | 30 | 2.28 | 68.4 | 2.4 |
| Rinsing 4 | 30 | 1.71 | 51.3 | 1.8 |
| Rinsing 5 | 30 | 1.16 | 34.8 | 1.2 |
| Rinsing 6 | 30 | 0.91 | 27.3 | 1 |
| Rinsing 7 | 30 | 0.91 | 27.3 | 1 |
| Filtered pool | 385 | 6.95 | 2675.8 | 93.3 |

By reducing the load volume on the filter and by rinsing the precipitate with a washing volume equivalent to the volume of product to be clarified (180 mL), no clogging is observed and the totality of the immunoglobulins was recovered. The totality of the immunoglobulins is available for the affinity chromatography step which follows in the purification method.

Example 8

Improvement in Putting the IgG Back into Solution

Upon making pilot size batches according to the novel method as described in Example 2, comparison with the batch prepared according to the method described in patent application EP1385886 at the same scale (10AXTO1064015) shows that it is possible to improve the putting of the « I+II+III» precipitate back into solution. Indeed, a difference of at least 1 g/L of IgG is observed in this step (the volumes being equivalent) as demonstrated by the table below.

| Putting back into a non-filtered solution | | | |
|---|---|---|---|
| Pilot size batch prepared according to the method described in patent application EP1385886 (g/L)* | Pilot size batches prepared according to the method of the invention (g/L) | | |
| | Batch 1* | Batch 2 | Batch 3 |
| 12.8 | 11.6 | 10.3 | 11.7 |

*Batches made with the same precipitate

Complementary tests have shown that, advantageously, it is possible to put the immunoglobulins present in the precipitate back into solution with a solution containing ions rather than with purified water. In particular, by using a 10 mM NaCl solution.

Moreover, the precipitation of protein contaminants with caprylic acid may also be improved at pHs of less than 4.8. In particular, a pH of 4.6 allows this improvement.

A pilot size batch (« novel batch» ) was made by taking into account these improvements and compared with the « Robust Chromatography Eluate» stage with the three batches (batches 1, 2 and 3) already made according to the invention.

The table below accounts for these differences:

| Yield of the novel method at the « Fluidized bed chromatography eluate » stage | | | | |
|---|---|---|---|---|
| | Novel batch | Batch 1 | Batch 2 | Batch 3 |
| pH of RES | 4.6 | 4.8 | 4.8 | 4.8 |
| g IgG/L plasma | 6.00 | 5.96 | 5.62 | 5.77 |
| IgG/proteins | 0.910 | 0.820 | 0.812 | 0.893 |

The novel batch made with putting back into solution with a solution having a 10 mM NaCl concentration, treated by caprylic acid and adjusted to a pH equal to 4.6, has:

better yield of immunoglobulins per liter of plasma applied, better purity as regards the immunoglobulins-total proteins ratio Example 9

Application of the Invention to the « II+III» Precipitate

The "II+III" precipitate is an alternative to the "I+II+III" precipitate as a source of raw material for purification of polyclonal IgGs.

On this basis, two batches according to the invention were made from different « II+III» precipitates. The results of the first evaluations obtained from both of these raw materials were compared to the "fluidized bed chromatography eluate" stage.

The table below accounts for these results:

|  | Batch «I + II + III» | Batch «II + III» | Batch «II + III» |
|---|---|---|---|
| pH of RES | 4.6 | 4.6 | 4.6 |
| g IgG/L of plasma | 6.00 | 5.17 | 5.1 |
| Purification yield % | 98 | 88 | 95 |
| IgG/proteins | 0.910 | 0.837 | 0.859 |

These results show that first steps of the method of the invention are performed in an equivalent way with both types of precipitate:

- as regards extraction yield: the cumulated yields of the clarification and robust affinity chromatography steps are comparable even if one of the batches is a little set back. However, the «II+III» precipitates which have undergone an additional fractionation step with ethanol as compared with the «I+II+III» precipitate have a yield in grams of IgG/L of plasma of 15% less than the one obtained with the «I+II+III» precipitate. This deficit is related to a loss of a portion of the IgGs during the additional fractionation step with ethanol.
- as regards purity: the IgG/total proteins ratios obtained with the «II+III» precipitates put back into solution, treated by caprylic acid and adjusted to a pH of 4.6 are comparable with those obtained with the «I+II+III» precipitates put back into solution, treated by caprylic acid and adjusted to a pH of 4.8.

The invention claimed is:

1. A method for preparing a concentrate of human polyvalent immunoglobulins from an initial solution of blood plasma or a fraction of plasma enriched with immunoglobulins, comprising:
    (a) removing protein contaminants by contacting the initial solution of blood plasma or a fraction of plasma enriched with immunoglobulins with caprylic acid in order to obtain a solution free of proteases, wherein the concentration of caprylic acid ranges from 0.5 to 1.5% by volume of caprylic acid per volume of initial solution of blood plasma or a fraction of plasma enriched with immunoglobulins to be treated, and
    (b) fluidized bed chromatography of the mixed-mode type of the solution free of proteases, to obtain a concentrate of human polyvalent immunoglobulins with a yield of more than 4.5 g of immunoglobulins per liter of blood plasma.

2. The method according to claim 1, wherein the step for removing protein contaminants with caprylic acid (a) is carried out at a pH between 4.3 and 4.9.

3. The method according to claim 2, wherein the step for removing protein contaminants with caprylic acid (a) is carried out at a pH between 4.6 and 4.8.

4. The method according to claim 1, further comprising between the step for removing protein contaminants with caprylic acid (a) and the fluidized bed chromatography step (b), a clarification step at an acid pH.

5. The method according to claim 4, wherein the clarification step is by depth filtration.

6. The method according to claim 1, wherein the fluidized bed chromatography step of the mixed-mode type comprises:
    loading on a chromatography column equilibrated beforehand with a buffer at a pH between 4.5 and 8, the solution having undergone the clarification step by depth filtration, adjusted beforehand to the same pH,
    washing the loaded column with a buffer solution until all non-adsorbed proteins on the column are removed,
    eluting polyvalent immunoglobulins adsorbed on the column with an elution buffer adjusted to a pH between 8 and 10, and
    recovering the solution enriched with human polyvalent immunoglobulins.

7. The method according to claim 1 further comprising, after step (b), one or more of the following steps:
    (i) a viral inactivation step,
    (ii) a step for anion exchange chromatography of the solution obtained at the end of step (i),
    (iii) a step for removing anti-A and anti-B antibodies from the solution obtained at the end of step (ii),
    (iv) a filtration step through nanometric filters with decreasing porosity from 100 to 15 nm,
    (v) a concentration step by ultrafiltration of the solution from step (iv) associated with a formulation step,
    (vi) and then a conventional sterilizing filtration step.

8. The method according to claim 1, wherein the initial solution is a plasma fraction enriched with immunoglobulins by fractionation with ethanol or by separation with chromatography.

9. The method according to claim 8, wherein the initial solution is a I+II+III precipitate or a II+III precipitate obtained from blood plasma fractionated with ethanol, and put back into solution.

10. The method according to claim 9, wherein the I+II+III precipitate or the II+III precipitate is put back into solution in purified water for injection or in a solution containing ions.

11. The method according to claim 10, wherein the solution containing ions is a solution comprising NaCl at a concentration of less than or equal to 20 mM.

12. The method according to claim 11, wherein the solution containing ions is a solution comprising NaCl at a concentration between 5 and 15 mM.

13. The method according to claim 12, wherein the solution containing ions is a solution comprising NaCl at a concentration equal to 10 mM.

14. The method according to claim 9, wherein the I+II+III precipitate or the II+III precipitate is treated with $CaCl_2$ solution, the concentration of which is less than or equal to 20 mM.

15. The method according to claim 14, wherein the I+II+III precipitate or the II+III precipitate is treated with $CaCl_2$ solution, the concentration of which is between 5 and 15 mM.

16. The method according to claim 15, wherein the I+II+III precipitate or the II+III precipitate is treated with a 10 mM $CaCl_2$ solution.

17. The method according to claim 1, comprising:
    (i) a step for removing protein contaminants with caprylic acid,
    (ii) a clarification step by depth filtration,
    (iii) a fluidized bed chromatography step of the "mixed-mode" type,
    (iv) a viral inactivation step with solvent/detergent treatment,
    (v) an anion exchange chromatography step,
    (vi) a step for removing anti-A and anti-B antibodies,
    (vii) filtration through nanometric filters with decreasing porosity from 100 to 15 nm,
    (viii) a step for concentrating by ultrafiltration the solution from the preceding step associated with a formulation step, and then a conventional sterilizing filtration step.

18. The method according to claim 1, further comprising the following steps:
- (a) adding to the concentrate of human polyvalent immunoglobulins obtained according to claim 1, one or several pharmaceutically acceptable stabilizers, and
- (b) optionally, freezing or freeze-drying the pharmaceutical preparation obtained in the preceding step;

so that the pharmaceutical preparation is in a liquid, frozen or freeze-dried form.

19. The method according to claim 1, wherein the concentration of caprylic acid ranges from 0.8 to 1.2%.

20. The method according to claim 19, wherein the concentration of caprylic acid ranges from 0.9 to 1.1%.

21. A method for preparing a concentrate of human polyvalent immunoglobulins from an initial solution of blood plasma or a fraction of plasma enriched with immunoglobulins, comprising:
- (a) removing protein contaminants by contacting the initial solution of blood plasma or the fraction of plasma enriched with immunoglobulins with caprylic acid in order to obtain a solution free of proteases, wherein the concentration of caprylic acid ranges from 0.9 to 1.1% by volume of caprylic acid per volume of initial solution of blood plasma or the fraction of plasma enriched with immunoglobulins to be treated, and
- (b) fluidized bed chromatography of the mixed-mode type of the solution free of proteases, to obtain a concentrate of human polyvalent immunoglobulins with a yield of more than 4.5 g of immunoglobulins per liter of blood plasma.

* * * * *